(12) United States Patent
Miller

(10) Patent No.: US 8,114,088 B2
(45) Date of Patent: Feb. 14, 2012

(54) GEARED SPINAL IMPLANT INSERTER-DISTRACTOR

(75) Inventor: Peter Thomas Miller, Austin, TX (US)

(73) Assignee: Zimmer Spine, Inc., Minneapolis, MN (US)

( * ) Notice: Subject to any disclaimer, the term of this patent is extended or adjusted under 35 U.S.C. 154(b) by 751 days.

(21) Appl. No.: 12/234,151

(22) Filed: Sep. 19, 2008

(65) Prior Publication Data

US 2010/0076557 A1    Mar. 25, 2010

(51) Int. Cl.
*A61B 17/58* (2006.01)
*A61F 2/44* (2006.01)

(52) U.S. Cl. ............ 606/90; 606/99; 623/17.11

(58) Field of Classification Search ............ 623/17.11; 606/90–108
See application file for complete search history.

(56) References Cited

U.S. PATENT DOCUMENTS

| | | | |
|---|---|---|---|
| 3,486,505 | A | 12/1969 | Morrison |
| 4,502,160 | A | 3/1985 | Moore |
| 4,697,586 | A | 10/1987 | Gazale |
| 4,931,055 | A | 6/1990 | Bumpus et al. |
| 5,397,364 | A | 3/1995 | Kozak et al. |
| 5,431,658 | A | 7/1995 | Moskovich |
| 5,704,938 | A | 1/1998 | Staehlin et al. |
| 6,033,405 | A | 3/2000 | Winslow et al. |
| 6,045,579 | A | 4/2000 | Hochshuler et al. |
| 6,080,193 | A | 6/2000 | Hochshuler et al. |
| 6,126,660 | A | 10/2000 | Dietz |
| 6,200,322 | B1 | 3/2001 | Branch et al. |
| 6,409,766 | B1 | 6/2002 | Brett |
| 6,478,800 | B1 | 11/2002 | Fraser et al. |
| 6,569,168 | B2 | 5/2003 | Lin |
| 6,576,016 | B1 | 6/2003 | Hochshuler et al. |
| 6,641,614 | B1 | 11/2003 | Wagner et al. |
| 6,648,895 | B2 | 11/2003 | Burkus |
| 6,652,533 | B2 | 11/2003 | O'Neil |

(Continued)

FOREIGN PATENT DOCUMENTS

AU    2003220366 B2    9/2003

(Continued)

OTHER PUBLICATIONS

Knight et al., An Introduction to Open Anterior Lumbar Interbody Fusion (ALIF); Indications, Approaches, Techniques, and Nursing Care, www.spineuniverse.com, Aug. 6, 2007, 5 pages.

(Continued)

*Primary Examiner* — Suzette J Gherbi
(74) *Attorney, Agent, or Firm* — Sprinkle IP Law Group

(57) ABSTRACT

Embodiments of a geared spinal implant inserter-distractor disclosed herein provide a greater mechanical advantage in delivering an intervertebral implant via an anterior, anterior-lateral, or posterior approach. The geared spinal implant inserter-distractor comprises an inserter, a distractor structured to slidably receive the inserter with a collar and an intervertebral implant attached thereto, and a gear mechanism arranged to translate a surgeon's rotational motion into linear motion, allowing the surgeon to have a greater control and feedback when placing an implant within an intervertebral disc space. The gear arrangement comprises a pinion inside the distractor and a rack on the inserter. The pinion can be driven by a shaft connected to a knob or handle. With the gear mechanism, a surgeon can turn the knob or handle to drive the inserter in and out of the distractor in a quantifiable manner, which facilitates the desirable precision delivery of the intervertebral implant.

18 Claims, 9 Drawing Sheets

U.S. PATENT DOCUMENTS

| | | |
|---|---|---|
| 6,663,637 B2 | 12/2003 | Dixon et al. |
| 6,676,668 B2 | 1/2004 | Mercereau et al. |
| 6,706,070 B1 | 3/2004 | Wagner et al. |
| 6,752,832 B2 | 6/2004 | Neumann |
| 6,755,841 B2 | 6/2004 | Fraser et al. |
| 6,893,464 B2 | 5/2005 | Kiester |
| 7,118,580 B1 | 10/2006 | Beyersdorff et al. |
| 2003/0014115 A1 | 1/2003 | Ralph et al. |
| 2003/0233145 A1 | 12/2003 | Landry et al. |
| 2004/0030387 A1 | 2/2004 | Landry et al. |
| 2004/0167535 A1 | 8/2004 | Errico et al. |
| 2005/0165408 A1 | 7/2005 | Puno et al. |
| 2006/0030856 A1 | 2/2006 | Drewry et al. |
| 2006/0167461 A1 | 7/2006 | Hawkins et al. |
| 2007/0123904 A1* | 5/2007 | Stad et al. ............ 606/99 |
| 2008/0071284 A1 | 3/2008 | Lechmann et al. |
| 2008/0091211 A1 | 4/2008 | Gately |
| 2008/0177275 A1* | 7/2008 | Wing et al. ............ 606/99 |
| 2010/0030283 A1* | 2/2010 | King et al. ............ 606/86 A |
| 2010/0191241 A1* | 7/2010 | McCormack et al. ...... 606/83 |
| 2011/0172722 A1* | 7/2011 | Verhulst et al. ......... 606/86 A |
| 2011/0172770 A1* | 7/2011 | Michelson ............ 623/17.11 |

FOREIGN PATENT DOCUMENTS

| | | |
|---|---|---|
| CA | 2 478 311 A1 | 9/2003 |
| DE | 603 14 096 T2 | 1/2008 |
| EP | 0 676 176 A1 | 10/1995 |
| EP | 1 482 877 A2 | 12/2004 |
| EP | 1 482 877 B1 | 5/2007 |
| ES | 2 287 460 T3 | 12/2007 |
| WO | WO 01/19295 A1 | 3/2001 |
| WO | WO 03/077808 A2 | 9/2003 |
| WO | WO 2006/014761 A1 | 2/2006 |

OTHER PUBLICATIONS

Janssen et al., Outcomes of Allogenic Cages in ALIF and PLIF: Biological Fusion Cages, www.spineuniverse.com, Nov. 12, 2003, 3 pages.

* cited by examiner

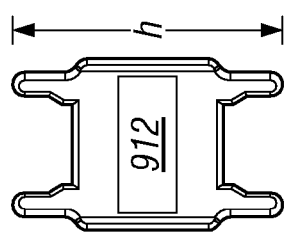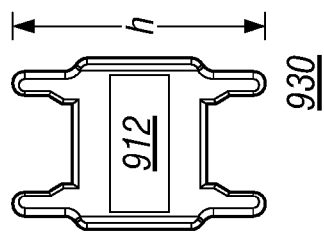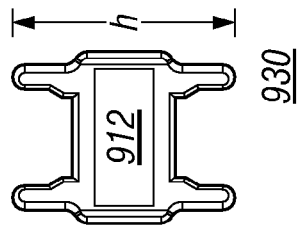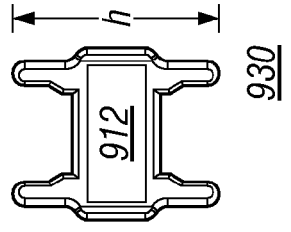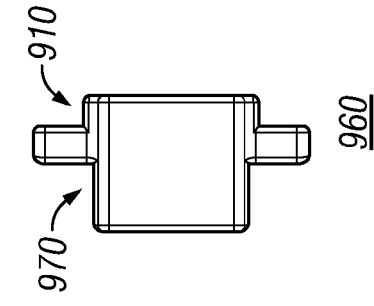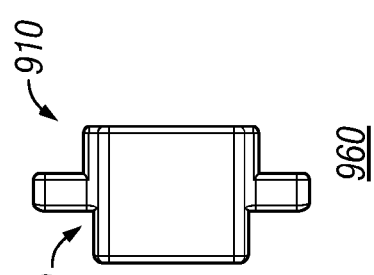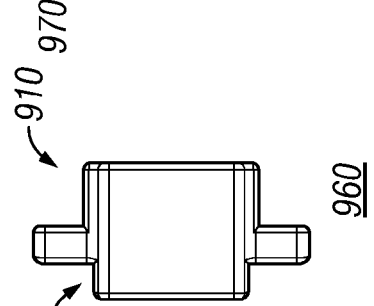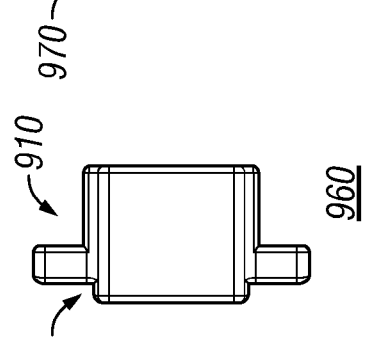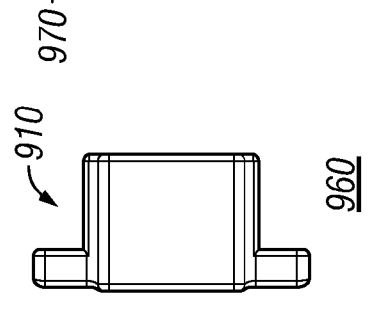

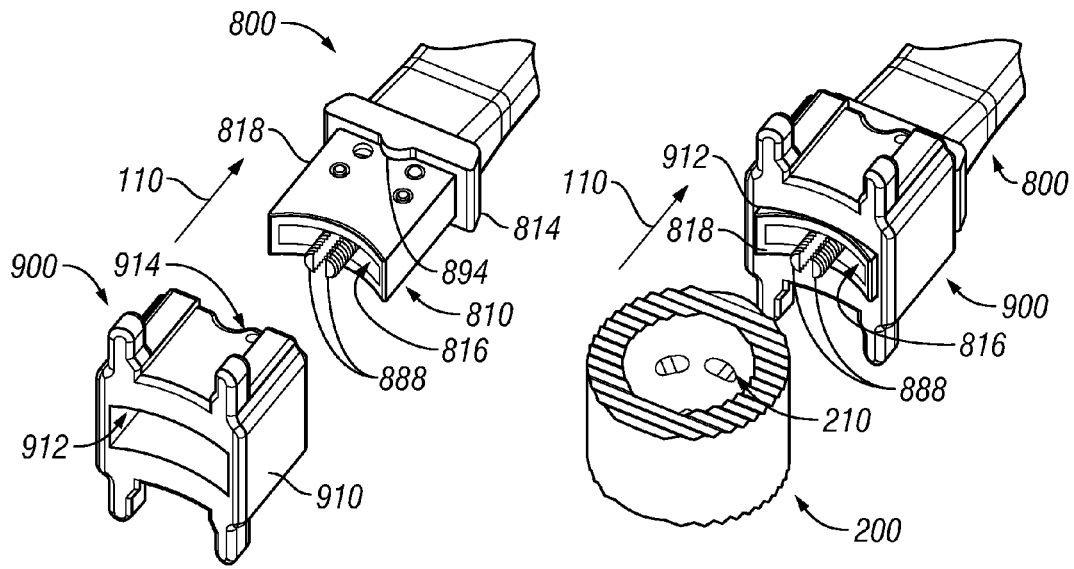
FIG. 10A
FIG. 10B
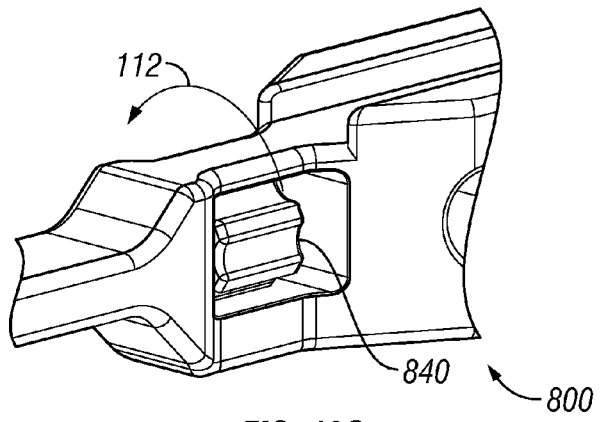
FIG. 10C
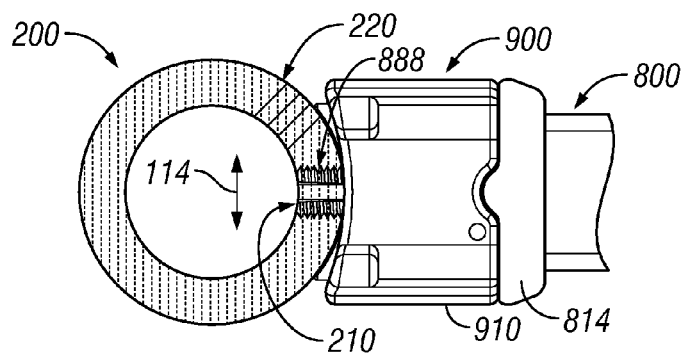
FIG. 10D

GEARED SPINAL IMPLANT INSERTER-DISTRACTOR

TECHNICAL FIELD OF THE DISCLOSURE

Embodiments of the disclosure relate generally to instruments for spine surgery. More particularly, embodiments of the disclosure relate to an implant inserter-distractor instrument useful for delivering an interbody device. Even more particularly, embodiments of the disclosure relate to a geared spinal implant inserter-distractor for delivering a bone graft via an anterior, anterior-lateral, or a posterior approach.

BACKGROUND OF THE RELATED ART

The human spine consists of segments known as vertebrae linked by intervertebral disks and held together by ligaments. There are 24 movable vertebrae—7 cervical (neck) vertebrae, 12 thoracic (chest) vertebrae, and 5 lumbar (back) vertebrae. Each vertebra has a somewhat cylindrical bony body (centrum), a number of winglike projections (processes), and a bony arch. The arches are positioned so that the space they enclose forms the vertebral canal. The vertebral canal houses and protects the spinal cord, and within it the spinal fluid circulates. Ligaments and muscles are attached to various projections of the vertebrae. The bodies of the vertebrae form the supporting column of the skeleton. Fused vertebra make up the sacrum and coccyx, the very bottom of the vertebral column.

The spine is subject to abnormal curvature, injury, infections, tumor formation, arthritic disorders, and puncture or slippage of the cartilage disks. Modern spine surgery often involves the use of spinal stabilization/fixation procedures such as a vertebral body fusion procedure to correct or treat various acute or chronic spine disorders and/or to support the spine. These procedures may utilize a variety of spinal implants to help stabilize the spine, correct deformities of the spine such as spondylolisthesis or pseudarthrosis, provide rigid support for an effected region of the spine, facilitate fusion, or treat spinal fractures. For example, anterior lumbar interbody fusion (ALIF) is a surgical technique that utilizes interbody implants to treat a variety of spinal disorders, including disc degeneration.

An intervertebral disc may be subject to degeneration caused by trauma, disease, and/or aging. An intervertebral disc that becomes degenerated may have to be partially or fully removed from a spinal column. Partial or full removal of an intervertebral disc may destabilize the spinal column, resulting in subsidence or deformation of vertebrae. Moreover, destabilization of a spinal column may result in alteration of a natural separation distance between adjacent vertebrae. As one skilled in the art can appreciate, excessive pressure applied to the nerves may cause pain and/or nerve damage. Maintaining the natural separation between vertebrae can help to prevent pressure from being applied to nerves that pass between vertebral bodies.

Through an ALIF procedure, a spinal implant may be inserted within a space created by the removal or partial removal of an intervertebral disc between adjacent vertebrae to maintain the height of the spine and restore stability to the spine. Such a spinal implant may be a fusion device that is designed to fuse with adjacent vertebrae through intervertebral bone growth. An interbody cage is an example of a fusion device. Some interbody cages of different designs have been developed to provide mechanical support to the segment being fused with biocompatible implant material and to allow the use of autogenous bone to promote fusion. Other types of spinal implant may also be used. For example, a bone graft may be inserted into an intervertebral disc space during a spinal fixation procedure using an anterior, lateral, or posterior spinal approach. Such a bone graft may be machined to different shapes, contours, sizes, and heights. A preoperative planner can aid in determining the size of the adjacent intervertebral discs and allow the implant to be firmly seated with a secure fit between the endplates. The surface of the bone graft may contain a saw-tooth pattern on the superior and inferior surfaces to minimize migration after implantation.

An anterior spinal approach may be a preferred method for some spinal implant procedures. An anterior spinal approach may require less bone removal and muscle distraction than a posterior spinal approach. In addition, an anterior spinal approach may involve less risk of nerve damage than a posterior spinal approach.

During an anterior spinal approach, a surgical opening may be made in the abdomen of a patient. This opening may extend from the abdomen to an anterior surface of the spine. For some patients, the opening may be ten or more inches in depth. The opening, sometimes referred to as the work site, needs to be large enough to accommodate instrumentation for inserting a spinal implant within a disc space. A discectomy may be performed to remove all or most of a defective or damaged intervertebral disc. The discectomy creates a disc space for a spinal implant. The amount of removed disc material may correspond to the size and type of a spinal implant to be inserted.

Once the work site has been prepared for device insertion, several surgical techniques can be used to distract, size, and insert the spinal implant, depending upon the patient's local anatomy, the pathology, and the surgeon's preference. One method for inserting a spinal implant within a disc space may include distracting the vertebrae with a distraction device to spread open the collapsed disc space and form a disc space that is slightly larger than a height of the implant to be inserted into the disc space. The implant is then inserted into the disc space using an implant holder or an implant insertion device. After the spinal implant is inserted, the distraction device may then be removed.

Another method involves the use of interbody spacers or trials. For example, surgical personnel may distract the vertebrae to obtain the maximum implant height using a distractor and insert a spacer into the disc space to ensure accurate sizing of the spinal implant. Fluoroscopy and tactile judgment can assist in confirming the fit and placement of the spacer. If the spacer is either too loose or too tight, the next size may be used to achieve the desired secure fit. Once the correct sizing is obtained, the spacer can be removed and the spinal implant can be introduced in the correct orientation into the disc space using an implant holder. After the spinal implant is inserted, the distractor may then be removed.

SUMMARY OF THE DISCLOSURE

Embodiments disclosed herein provide a surgical instrument that integrates multiple functions to provide the surgical personnel a way to efficiently and accurately deliver an intervertebral implant into a disc space between adjacent vertebrae. More particularly, embodiments disclosed herein provide a geared spinal implant inserter-distractor useful for delivering an intervertebral implant into a collapsed disc space. Embodiments of the geared spinal implant inserter-distractor may be utilized in various surgical procedures, including anterior lumbar interbody fusion (ALIF) via an anterior or anterior-lateral approach, posterior lumbar interbody fusion (PLIF) via a posterior approach, transforaminal lumbar interbody fusion (TLIF) via a posterior-lateral approach, and anterior cervical discectomy and fusion (ACDF), etc.

In some embodiments, the intervertebral implant can be an interbody device or a bone graft. In some embodiments, the bone graft is an allogenic graft, also known as allograft. In some embodiments, a geared spinal implant inserter-distractor comprises an inserter component, a distractor component, and a collar. In some embodiments, the body of the distractor component has an opening structured to receive the inserter component with a collar and an intervertebral implant attached thereto.

Embodiments of a geared spinal implant inserter-distractor disclosed herein further comprise a geared mechanism with gears arranged to translate rotational motion into linear motion, allowing a surgeon to have a greater control and feedback when placing an intervertebral implant within an intervertebral disc space between adjacent vertebrae.

In some embodiments, the geared mechanism of a geared spinal implant inserter-distractor disclosed herein comprises a pair of gears. In some embodiments, the geared mechanism of a geared spinal implant inserter-distractor disclosed herein comprises a pinion (i.e., a small gear) positioned inside the distractor component and a rack form on the outside of the inserter component. In some embodiments, the inserter component has an opening or cavity which allows a shaft to travel a certain distance parallel to the rack. In some embodiments, the rack resembles a toothed bar or rod. The teeth of the rack mesh with the teeth of the pinion. The shaft connects the pinion to a knob or handle located on the outside of the distractor component. In some embodiments, the shaft can be pushed into the opening or cavity of the inserter component via the knob or handle after the rack and the pinion are engaged. In some embodiments, the shaft has or connects to a hex end. In some embodiments, a standard hex driver or wrench can be coupled to the shaft. In some embodiments, the hex driver or wrench can function as a handle, a lever, or a crank to drive the pinion. In some embodiments, the shaft has a threaded end and a handle or the like can be screwed on to the threaded end of the shaft to drive the pinion. In some embodiments, the handle is detachable from the distractor component. In some embodiments, the handle is not detachable from the distractor component. In some embodiments, the handle is structured to resemble a clam shell. In some embodiments, the handle has a contour that matches a portion of the distractor component. In some embodiments, the handle can be folded down when not in use.

In some embodiments, a surgeon can turn a knob or crank a handle to drive the inserter component in and out of the distractor component. With the geared mechanism, the rotational motion of turning the knob or cranking the handle can be translated into linear motion in a quantifiable manner, which facilitates the desirable precision delivery of the intervertebral implant to the intervertebral disc space between adjacent vertebrae. The geared mechanism of the geared spinal implant inserter-distractor disclosed herein can also provide the surgical personnel with greater control and feel for the linear movement. By meshing a rack with a pinion, torque can be converted to linear force using less energy, making the geared spinal implant inserter-distractor disclosed herein easy to use.

In some embodiments, a method of delivering an intervertebral implant in an spinal implant procedure can include fitting a distractor component of a geared spinal implant inserter-distractor in a collapsed disc space between adjacent vertebrae, sliding a collar onto an end portion of an inserter component of the geared spinal implant inserter-distractor, closing inserter tangs at the end portion of the inserter component, placing the inserter tangs inside a hole of the intervertebral implant, spreading the inserter tangs to hold the intervertebral implant by tension, guiding the intervertebral implant, the collar, and the inserter component down the center of the distractor component, and gradually distracting the collapsed disc space between the adjacent vertebrae by applying a controlled rotating force onto a handle or knob of the geared spinal implant inserter-distractor to push the inserter component towards the collapsed disc space in a linear motion. The protruding features of the collar can guide and keep the intervertebral implant in alignment with the distractor component. As the surgical personnel turns the handle or knob, the body portion of the collar can push against the ramps of the distractor component to shield the intervertebral implant from compression loading until the intervertebral implant is delivered in a proper location between the adjacent vertebrae. The intervertebral implant thus delivered can restore lumbar disc height in the treatment of diseased or degenerative discs.

Embodiments of a geared spinal implant inserter-distractor disclosed herein can provide many advantages. Particularly, embodiments of a geared spinal implant inserter-distractor disclosed herein can overcome problems associated with delivering an implant into a collapsed disc space via impaction or sudden distraction. Impaction or sudden distraction may cause damage or unwanted results. For example, impacting an implant into a collapsed disc space may fracture one or both vertebrae and the implant itself. By gradually delivering an implant via a geared mechanism, embodiments of a geared spinal implant inserter-distractor disclosed herein can avoid risking fracturing the adjacent vertebrae. Moreover, by utilizing a collar in conjunction with the inserter-distractor components, embodiments of a geared spinal implant inserter-distractor disclosed herein can shield an implant from compression loading during delivery.

Other objects and advantages of the embodiments disclosed herein will be better appreciated and understood when considered in conjunction with the following description and the accompanying drawings.

BRIEF DESCRIPTION OF THE DRAWINGS

A more complete understanding of the present invention and the advantages thereof may be acquired by referring to the following description, taken in conjunction with the accompanying drawings in which like reference numbers indicate like features and wherein:

FIGS. 9C-9L depict views of various embodiments of a collar with different heights and countersink depths;

FIGS. 10A-10D illustrate one way of coupling a collar to an inserter component and then coupling an interbody implant thereto;

Figure 1:
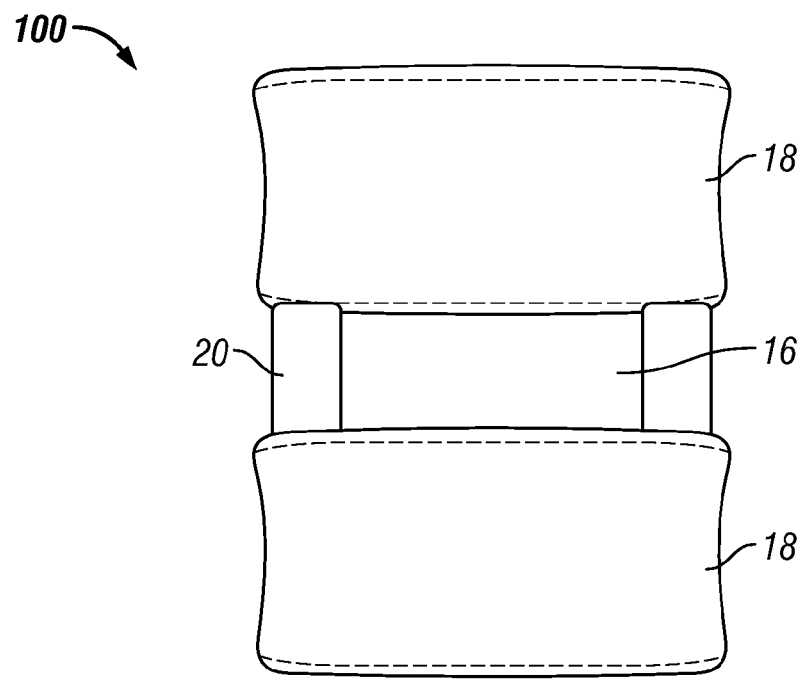
FIG. 1 depicts a portion of a spine with an intervertebral disc between adjacent vertebrae.

While this disclosure is susceptible to various modifications and alternative forms, specific embodiments thereof are shown by way of example in the drawings and will herein be described in detail. It should be understood, however, that the drawings and detailed description thereto are not intended to limit the disclosure to the particular form disclosed, but to the contrary, the intention is to cover all modifications, equivalents and alternatives falling within the spirit and scope of the present disclosure as defined by the appended claims.

DETAILED DESCRIPTION

Embodiments of a geared spinal implant inserter-distractor and the various features and advantageous details thereof are explained more fully with reference to the non-limiting embodiments detailed in the following description. Descriptions of well known starting materials, manufacturing techniques, components and equipment are omitted so as not to unnecessarily obscure the invention in detail. Skilled artisans should understand, however, that the detailed description and the specific examples, while disclosing preferred embodiments of the invention, are given by way of illustration only and not by way of limitation. Various substitutions, modifications, and additions within the scope of the underlying inventive concept(s) will become apparent to those skilled in the art after reading this disclosure. Skilled artisans can also appreciate that the drawings disclosed herein are not necessarily drawn to scale.

As used herein, the terms "comprises," "comprising," includes, "including," "has," "having" or any other variation thereof, are intended to cover a non-exclusive inclusion. For example, a process, product, article, or apparatus that comprises a list of elements is not necessarily limited to only those elements, but may include other elements not expressly listed or inherent to such process, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Additionally, any examples or illustrations given herein are not to be regarded in any way as restrictions on, limits to, or express definitions of, any term or terms with which they are utilized. Instead, these examples or illustrations are to be regarded as being described with respect to a particular embodiment and as illustrative only. Those of ordinary skill in the art will appreciate that any term or terms with which these examples or illustrations are utilized encompass other embodiments as well as implementations and adaptations thereof which may or may not be given therewith or elsewhere in the specification and all such embodiments are intended to be included within the scope of that term or terms. Language designating such non-limiting examples and illustrations includes, but is not limited to: "for example," "for instance" "e.g.," "in one embodiment," and the like.

FIG. 1 depicts a portion of spine 100 with intervertebral disc 20 between adjacent vertebrae 18. In some cases, intervertebral disc 20 may be collapsed or have a reduced disc height due to disease, age, injury, etc. Spinal fusion is a surgical procedure in which two or more vertebrae are joined or fused together in the treatment of spinal disorders such as spondylolisthesis, scoliosis, severe disc degeneration, spinal fractures, and so on. A bone graft, taken from a patient's pelvic bone (autograft) or from a donor (allograft), can be inserted between two adjacent vertebrae to facilitate fusion. To form disc space 16 into which such a bone graft can be inserted between adjacent vertebrae 18, a portion or all of intervertebral disc 20 may be removed during a discectomy.

Common fusion surgeries include Posterior Lumbar Interbody Fusion (PLIF) and Anterior Lumbar Interbody Fusion (ALIF). An ALIF procedure can be done from the front (anterior) or from the front side (anterior-lateral) of the body, usually through a small incision in the lower abdominal area. Through the incision, the surgical personnel can retract the abdominal muscles and blood vessels, access the vertebrae, and remove disc material. After the disc material is removed, the surgical personnel can then insert a bone graft (and anterior interbody cages, rods, or screws if necessary) to stabilized the spine and facilitate fusion.

Figure 2:
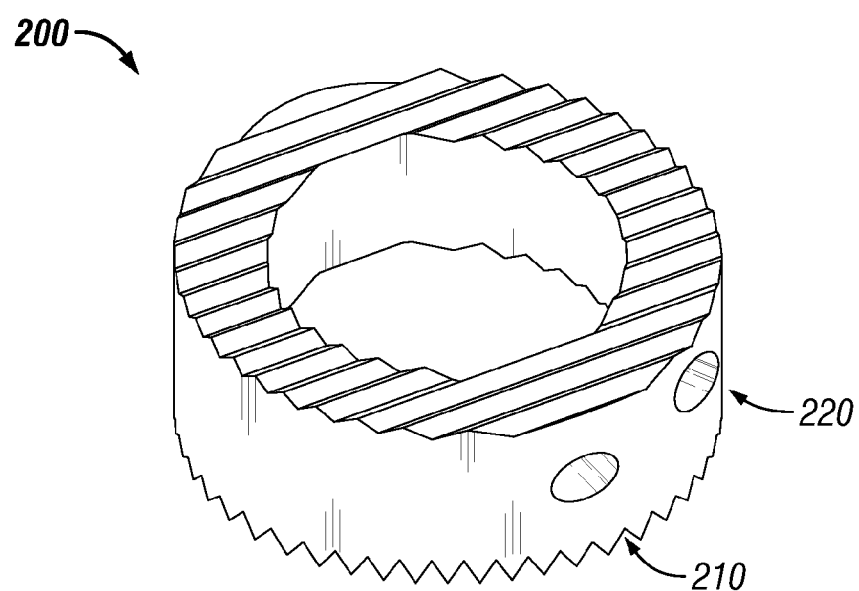
FIG. 2 depicts one example of a bone graft suitable to be inserted into an intervertebral disc space between adjacent vertebrae.

FIG. 2 depicts one example of implant 200 suitable to be inserted into intervertebral disc space 16 to restore lumbar disc height of intervertebral disc 20 in the treatment of diseased or degenerative discs. In some embodiments, implant 200 can be a bone graft. Bone graft 200 can be an autograft or an allograft. In some embodiments, implant 200 can be a bioengineered part. As one skilled in the art can appreciate, implant 200 can be made and/or machined to different shapes, contours, sizes, and heights. Accordingly, other configurations of implant 200 are possible and are not limited to what is shown in FIG. 2. In some embodiments, the superior and inferior surfaces of implant 200 may contain a saw-tooth pattern to help implant 200 to grab onto the inferior and superior surfaces of adjacent vertebrae 18 and minimize migration after implantation. As illustrated in FIG. 2, implant 200 may contain one or more lateral apertures, each of which is a hole or an opening in or through implant 200. As will be described in more details below, the hole(s) can facilitate the insertion and orientation of implant 200 during an ALIF procedure. In the example of FIG. 2, implant 200 has hole 210 for use in an anterior approach and hole 220 for use in an anterior-lateral approach. As one skilled in the art can appreciate, embodiments of a geared spinal implant inserter-distractor disclosed herein may be implemented to deliver various types of implants in different surgical procedures. Thus, implant 200 is not limited to what is shown in FIG. 2 and can be adapted for use in an ALIF, PLIF, TLIF, ACDF or other spinal fusion procedure.

Figure 3:
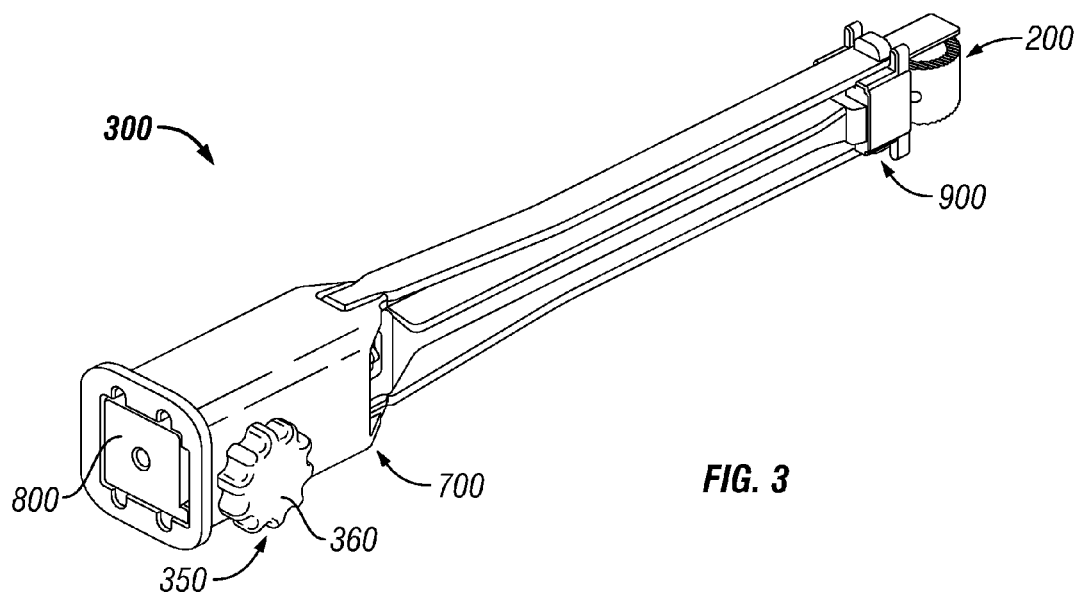
FIGS. 3-6 depict embodiments of a geared spinal implant distractor-inserter instrument suitable for delivering an implant via an anterior, anterior-lateral, or a posterior approach.

FIG. 3 depicts one embodiment of geared spinal implant distractor-inserter instrument 300 suitable for delivering implant 200 via an anterior or anterior-lateral approach. In this embodiment, geared spinal implant distractor-inserter instrument 300 comprises distractor component 700, inserter component 800, and geared mechanism 350. Geared mechanism 350 comprises a pair of gears and knob 360. A first gear inside distractor component 700 (see FIG. 7) meshes with a second gear on inserter component 800 (see FIG. 8A) and connects to knob 360 so that, once the gears are engaged, turning knob 360 can slide inserter component 800 in or out of distractor component 700. In some embodiments, knob 360 is detachable from geared mechanism 350. In some embodiments, knob 360 is not detachable from geared mechanism 350. FIG. 3 shows that distractor component 700 and inserter component 800 are fully engaged, with implant 200 detachably coupled to inserter component 800 and shielded from compression loading via collar 900.

Figure 4:
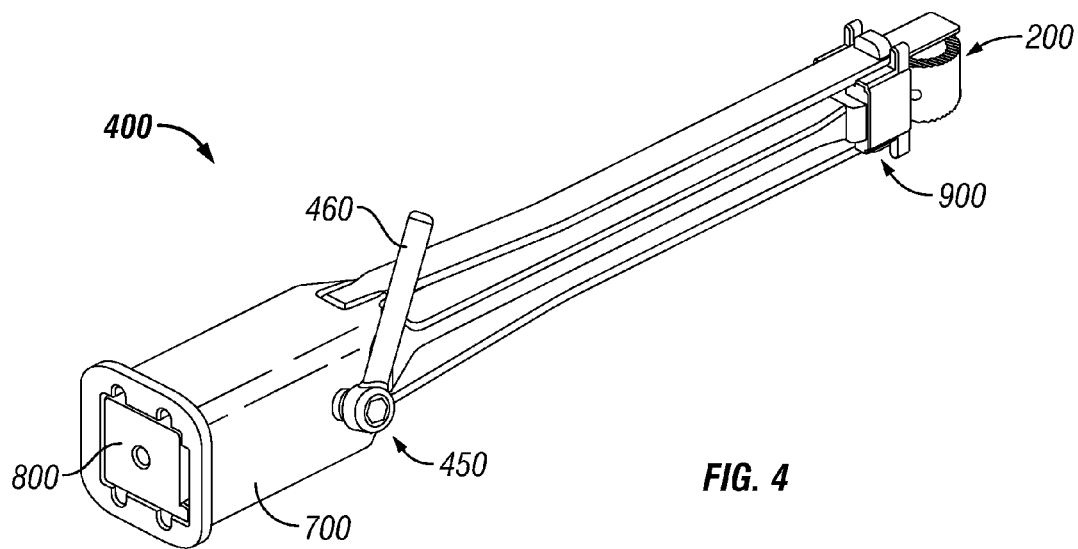

FIG. 4 depicts one embodiment of geared spinal implant distractor-inserter instrument 400 having distractor component 700, inserter component 800, and geared mechanism 450. In the example of FIG. 4, implant 200 is detachably coupled to inserter component 800 and shielded from compression loading via collar 900. Instead of a knob, geared mechanism 450 comprises handle 460 for driving a first gear inside distractor component 700. Once the first gear inside distractor component 700 engages a second gear on inserter component 800, turning handle 460 can move inserter component 800 in a linear direction relative to distractor component 700. In some embodiments, handle 460 is detachable from geared mechanism 450. In some embodiments, handle 460 is integral to geared mechanism 450 and not detachable from geared mechanism 450.

Figures 5, 6:
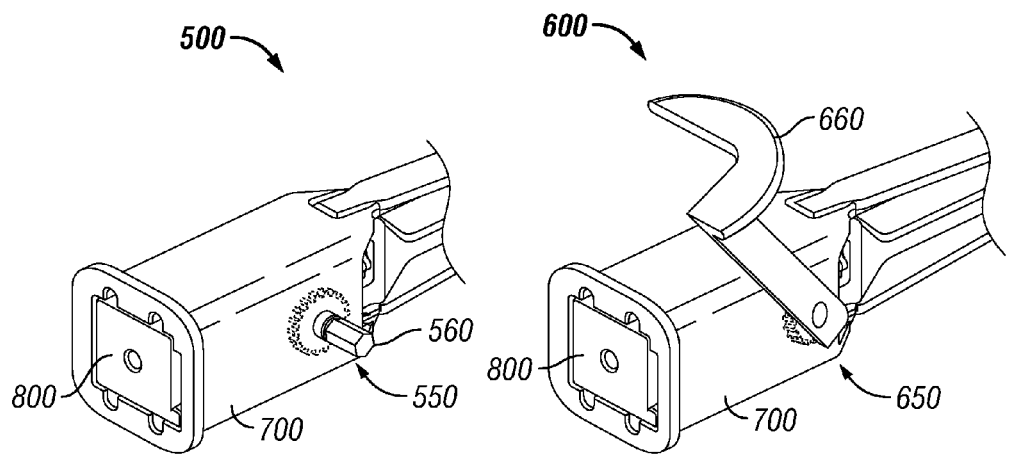

FIG. 5 depicts a portion of one embodiment of geared spinal implant distractor-inserter instrument 500 having distractor component 700, inserter component 800, and geared mechanism 550. In some embodiments, geared mechanism 550 comprises a stub or a small projection that projects from a side of distractor component 700 and that connects to a first gear inside distractor component 700. In the example of FIG. 5, stub 560 has a hexagonal shape and size. In some embodiments, a standard hex driver can be utilized to drive geared mechanism 550 via stub 560. Other stub-driver combinations are also possible and are not limited to what is shown in FIG. 5. For example, stub 560 can have a cavity or a through hole with an inner diameter sufficiently large to accept a rod or a shaft of a T-bar which can then be used as a handle or a lever to turn stub 560.

As one skilled in the art can appreciate, in some embodiments, geared spinal implant distractor-inserter instrument 500 can have a detachable handle coupled to geared mechanism 550 via stub 560. In some embodiments, geared spinal implant distractor-inserter instrument 500 can have a built-in handle coupled to geared mechanism 550 via stub 560. Similar to geared mechanisms 350 and 450 described above, parts of geared mechanism 550 are arranged so that the rotating force (torque) applied onto a driver, a handle, a lever, or a crank coupled to stub 560 is translated to the linear force that moves inserter component 800 in and out of distractor component 700. During the delivery of an intervertebral implant, the surgical personnel can move inserter component 800 either towards or away from the disc space depending on which direction stub 560 is rotated via a handle, a lever, a crank, a rod, a T-bar, or the like coupled thereto.

FIG. 6 depicts a portion of one embodiment of geared spinal implant distractor-inserter instrument 600 having distractor component 700, inserter component 800, geared mechanism 650, and built-in handle 660. Geared spinal implant distractor-inserter instrument 600 could have a split handle, either one sided or shaped like a clam shell as shown in FIG. 6, to drive geared mechanism 650 which, in turn, drives inserter component 800 in and out of distractor component 700. Embodiments of a geared spinal implant distractor-inserter instrument disclosed herein take the mechanical advantage gained by using a lever or the like. In some embodiments, marker(s) can be utilized in conjunction with gear and/or lever designs to provide the surgical personnel indications of starting and end points. As an example, when handle 660 of geared spinal implant distractor-inserter instrument 600 is in a first position, it may indicate an initial engagement of inserter component 800 and distractor component 700. When handle 660 of geared spinal implant distractor-inserter instrument 600 is in a second position, it may indicate that inserter component 800 and distractor component 700 are fully engaged. In the example shown in FIG. 6, inserter component 800 and distractor component 700 are shown to be fully engaged when handle 660 of geared spinal implant distractor-inserter instrument 600 is in an upward (open) position. In this case, turning handle 660 downwards (counterclockwise) moves inserter component 800 out of distractor component 700.

In one embodiment, inserter component 800 and distractor component 700 can be fully engaged when handle 660 of geared spinal implant distractor-inserter instrument 600 is in a closed position. In this case, handle 660 is initially in an upward position when inserter component 800 engages distractor component 700. In some embodiments, turning handle 660 downwards (counterclockwise) moves inserter component 800 into distractor component 700 and towards an intervertebral disc space during an ALIF procedure delivering implant 200. The starting point and end point of the rotational movement of handle 660 may vary from patient to patient or on a case-by-case basis. To facilitate the surgical personnel identifying appropriate starting and end points, embodiments of a geared spinal implant distractor-inserter instrument disclosed herein may provide visual indications that correspond to the internal interlinked arrangement.

Figure 7:
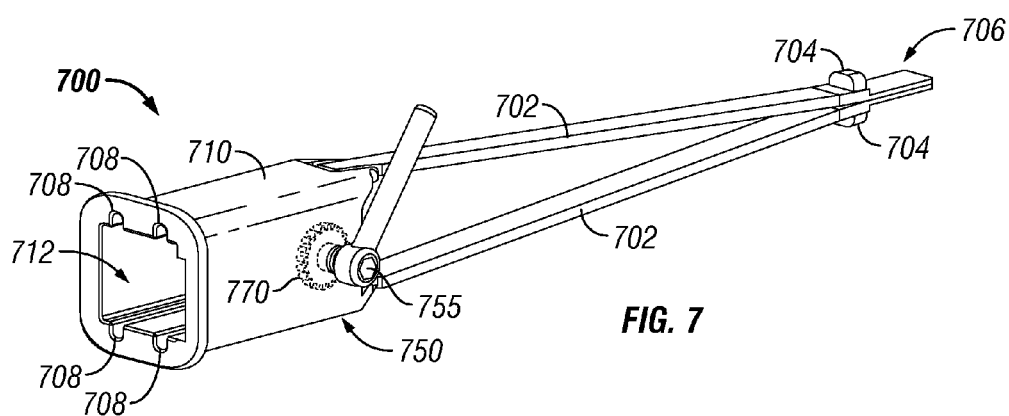
FIG. 7 depicts a perspective view of one embodiment of a distractor component of the geared spinal implant distractor-inserter instrument of FIGS. 3-6.

FIG. 7 depicts a perspective view of one embodiment of distractor component 700 comprising body 710 and two ramps 702. As illustrated in FIG. 7, each ramp 702 is coupled to body 710 at a first end. Each ramp 702 has tip 706 and stop 704 positioned between ramp 702 and tip 706. In some embodiments, tip 706 is thinner than ramp 702. In some embodiments, tip 706 may be integral to ramp 702 and made of the same material as ramp 702. Components of embodiments of a geared spinal implant distractor-inserter instrument disclosed herein may be made of any biocompatible material, including, but not limited to, titanium, titanium alloy, stainless steel, ceramic, polymers, or combinations thereof. In some embodiments, ramps 702 are made of stainless steel. In some embodiments, tip 706 may be reinforced with a stronger, more rigid material than that of ramp 702. In some embodiments, ramps 702 are attached to body 710. In some embodiments, ramps 702 are integrally formed with body 710. As shown in FIG. 7, when distractor component 700 is not in use with inserter component 800, tips 706 allow little or no space therebetween.

In some embodiments, body 710 of distractor component 700 can have a textured or an otherwise easy-to-grab exterior to allow a person to hold distractor component 700 in one hand while cranking the geared mechanism with the other hand. Body 710 of distractor component 700 has opening 712 dimensioned and shaped to receive inserter component 800. In some embodiments, opening 712 is particularly dimensioned and shaped to accommodate inserter component 800 with collar 900 and implant 200 attached thereto. For example, opening 712 can have features 708 extending through the length of body 710 to accommodate arms 908 of collar 900 (see FIGS. 9A and 9B). As illustrated in FIG. 7, opening 712 may not be symmetrical and can include groove(s) and/or recess area(s) to guide inserter component 800 and collar 900 and to accommodate gear 770 of geared mechanism 750. In the example shown in FIG. 7, gear 770 of geared mechanism 750 can be driven by turning stub 755 (via a lever, a handle, a driver, a wrench, or the like coupled to stub 755).

Figure 8A:
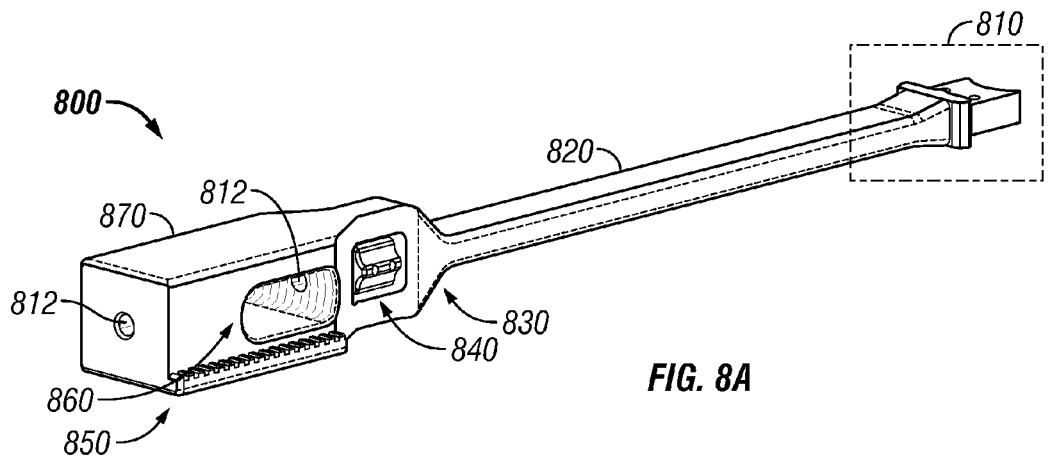
FIG. 8A depicts a perspective view of one embodiment of an inserter component of the geared spinal implant distractor-inserter instrument of FIGS. 3-6.

FIG. 8A depicts a perspective view of one embodiment of inserter component 800. In some embodiments, inserter component 800 can comprise body portion 870, neck portion 830, elongated portion 820, end portion 810, and through hole 812 that extends through body portion 870, neck portion 830, elongated portion 820, and end portion 810 about a central axis thereof. In some embodiments, portions 870, 830, 820, and 810 may be monolithically formed from a single material. In some embodiments, body portion 870 comprises opening 860 that extends through the width of body portion 870. In some embodiments, body portion 870 comprises opening 860 that is hollow within body portion 870 and that does not extend through the width of body portion 870.

In some embodiments, opening 860 allows a shaft (not shown) to travel a predetermined distance. In some embodiments, this predetermined distance corresponds to the maximum turning radius of stub 755. In some embodiments, stub 755 may travel between about 0 degree to about 160 degree or more. In some embodiments, body portion 870 further comprises rack 850. In some embodiments, rack 850 may comprise a plurality of teeth formed on the exterior of body portion 870 and substantially along the length of body portion 870. Although rack 850 is shown in FIG. 8A below opening 860, it can be appreciated that body portion 870 may have rack 850 located above opening 860 for opposite direction movement.

In some embodiments, the geared mechanism of a geared spinal implant distractor-inserter instrument includes a rack (i.e., a toothed bar or rod) on an inserter component, a pinion (i.e., a small gear) inside a distractor component, and a drive mechanism. Such a rack can be seen as a gear with an infinitely large radius of curvature. By meshing a rack with a pinion, the rotating force applied on the drive mechanism to turn the pinion can be translated into linear force that moves the rack in a straight line, up to the limit of its travel. As FIGS. 7 and 8A illustrate, both rack 850 on inserter component 800 and pinion 770 inside distractor component 700 have teeth that mesh with each other. As one skilled in the art can appreciate, there are many possible teeth sizes and configurations of a rack and pinion arrangement.

Figure 8B:
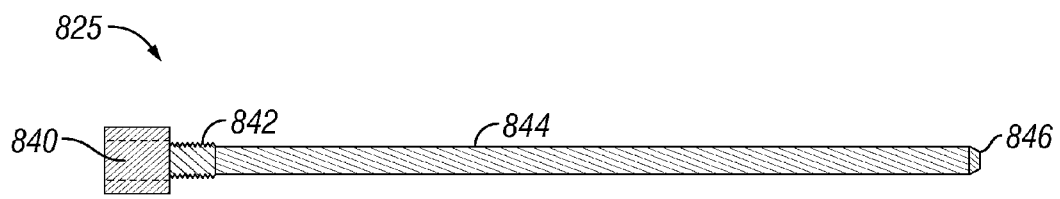
FIG. 8B depicts a cross-sectional view of an elongated member of the inserter component of FIG. 8A.

FIG. 8B depicts a cross-sectional view of elongated member 825 positioned inside elongated portion 820 of inserter component 800 of FIG. 8A. In this embodiment, elongated member 825 comprises shaft 844, threaded end 842, and tapered end 846. As illustrated in FIG. 8B, shaft 844 may be coupled to turn knob 840 via threaded end 842.

Figure 8C:
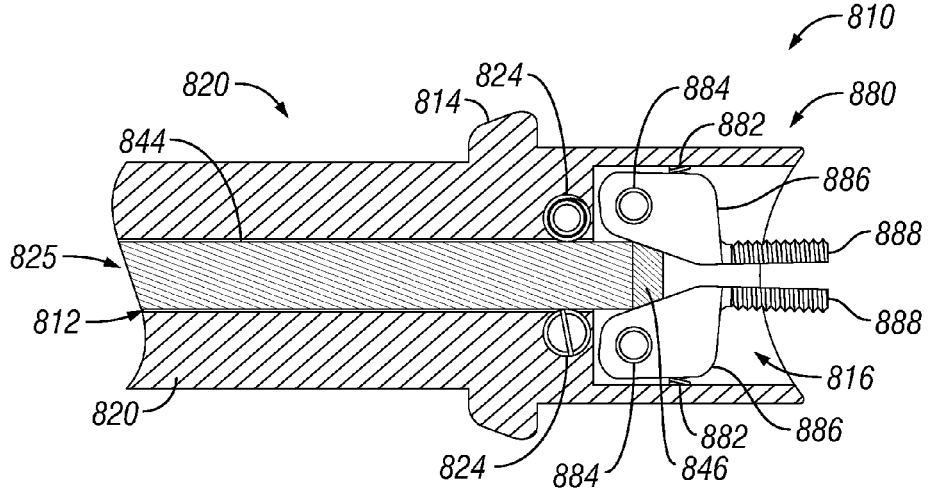
FIG. 8C depicts a cross-sectional close-up view of an end portion of the inserter component of FIG. 8A.

FIG. 8C depicts a cross-sectional close-up view of end portion 810 of inserter component 800 of FIG. 8A. As illustrated in FIG. 8C, flange 814 may be located between elongated portion 820 and end portion 810. End portion 810 may include holders 824 for holding on collar 900. End portion 810 may include opening or cavity 816 inside which gates 886 are located proximate to through hole 812 where end 846 of shaft 844 of elongated member 825 may exit. Each gate 886 pivots about point 884 and comprises threaded end 888. End portion 810 further comprises springs 882 that force gates 886 to close in its natural state. When gates 886 are closed, inserter tangs 888 form a cylindrical body with an outer diameter sufficiently small to fit inside of hole 210 or hole 220 of implant 200. As FIG. 8C exemplifies, advancing end 846 of shaft 844 of elongated member 825 towards end portion 810 can cause gates 886 to open which, in turn, cause inserter tangs 888 to become separated. Thus, turning turn knob 840 in a first direction can cause inserter tangs 888 to close and fit inside hole 210 or hole 220 of implant 200 and, when inserter tangs 888 are inside hole 210 or hole 220, turning turn knob 840 in a second direction can cause inserter tangs 888 to spread and hold implant 200 in position by tension. In this way, implant 200 can be securely attached to end portion 810 by advancing elongated member 825 to open gates 886 and push inserter tangs 888 against the walls inside hole 210 in an anterior approach and inside hole 220 in an anterior-lateral approach.

Figure 9A:
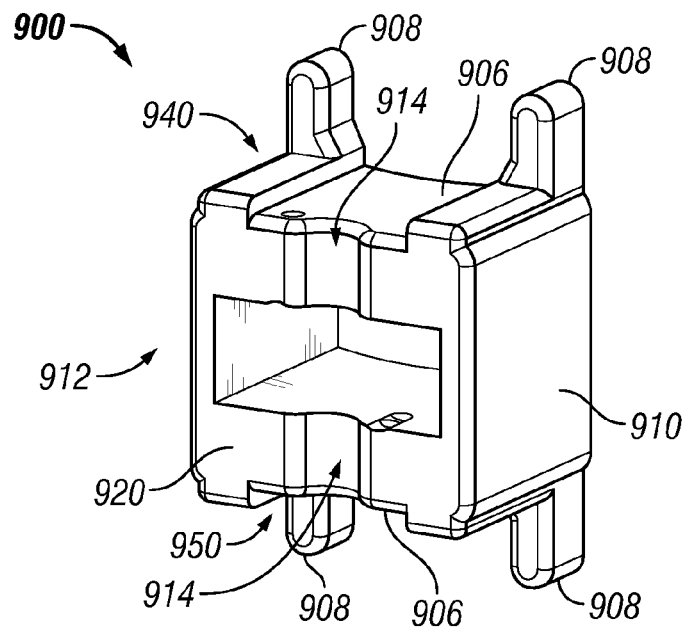
FIGS. 9A-9B depict perspective views of one embodiment of a collar.
Figure 9B:
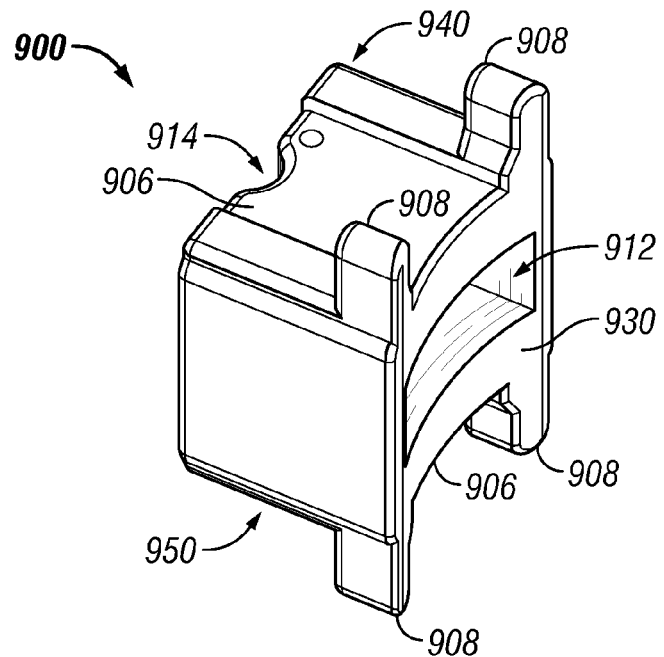

FIGS. 9A-9B depict front and back perspective views of one embodiment of collar 900. Collar 900 can comprise body 910 and protruding features or ears 908. Ears 908 can ensure that the geared spinal implant distractor-inserter instrument stops at a desired position when delivering an intervertebral implant to a collapsed disc space. Body 910 of collar 900 can have front surface 920, back surface 930, superior surface 940, inferior surface 950, and opening 912. Referring also to FIGS. 10A-10D, opening 912 of collar 900 is dimensioned and sized to accept tip 818 of end portion 810 of inserter component 800. In some embodiments, front surface 920 may have recess areas 914 to accommodate bumps 894 of flange 814 located between elongated portion 820 and end portion 810 of distractor component 800. In some embodiments, back surface 930 of collar 900 may be curved to accommodate implant 200. In some embodiments, superior surface 940 and inferior surface 950 can include indentations or channels 906 to guide and keep the two distractor arms (see ramps 702 of distractor component 700 of FIG. 7) in alignment.

FIGS. 9C-9G depict back views of various embodiments of collar 900 with different heights h. In some embodiments, the height and configuration of ears 908 and the dimensions of opening 912 remain unchanged. FIG. 9C shows one embodiment of a 11 mm collar. FIG. 9D shows one embodiment of a 13 mm collar. FIG. 9E shows one embodiment of a 15 mm collar. FIG. 9F shows one embodiment of a 17 mm collar. FIG. 9G shows one embodiment of a 19 mm collar. Other collar heights are also possible.

FIGS. 9H-9L depict side views of various embodiments of collar 900 with different side profiles 960. In some embodiments, a countersink can be used to control the manner and depth in which collar 900 stops the geared spinal implant distractor-inserter instrument at a desired position when delivering an intervertebral implant to a collapsed disc space. FIG. 9H shows one embodiment of a collar with body 910 and no countersink 970. FIG. 9I shows one embodiment of a collar with 2 mm countersink 970 and correspondingly shorter body 910. FIG. 9J shows one embodiment of a collar with 4 mm countersink 970 and corresponding body 910. FIG. 9K shows one embodiment of a collar with 6 mm countersink 970 and corresponding body 910. FIG. 9L shows one embodiment of a collar with 8 mm countersink 970 and corresponding body 910. Other countersink depths are also possible. In some embodiments, countersink 970 can be built-in to collar 900 with corresponding depth marks on distractor component 700. Such depth marks can let the surgical personnel know how far inserter component 800 is in, which can be particularly useful for imaging during a spinal surgical procedure.

FIGS. 10A-10D illustrate one way of coupling collar 900 to inserter component 800 and then coupling implant 200 to inserter tangs 888 that stick out of tip 818 of end portion 810 of inserter component 800. Specifically, in some embodiments, a method of delivering an intervertebral implant can include coupling collar 900 to inserter component 800 in a direction indicated by arrow 110 with front surface 920 of collar 900 facing end portion 810 of inserter component 800 and aligning opening 912 of collar 900 with tip 818 of inserter component 800 as shown in FIG. 10A. Collar 900 can then be advanced towards inserter component 800 until front surface 920 of collar 900 engages flange 814 of inserter component 800 and recess areas 914 of collar 900 mate with bumps 894 of inserter component 800. The engagement of recess areas 914 of collar 900 and bumps 894 of inserter component 800 can reduce or prevent lateral movement of collar 900 relative to inserter component 800, further facilitating precision delivery of implant 200.

As FIG. 10B exemplifies, when collar 900 fully engages end portion 810 of inserter component 800, inserter tangs 888 stick out from opening 816 of tip 818. In some cases, a small part of tip 818 may be visible from opening 912 of collar 900. In FIG. 10B, implant 200 is shown to be coupled to end portion 810 of inserter component 800 via hole 210 in an anterior approach.

As described above, when inserter tangs 888 are closed, they can fit inside hole 210. By turning knob 840 of inserter component 800, the surgical personnel can manipulate inserter tangs 888 to make them close to fit inside hole 210 or open to hold implant 200 in place. In some embodiments, the manipulation of inserter tangs 888 can be achieved by advancing or retracting elongated member 825 inside elongated portion 820 of inserter component 800 in which advancing elongated member 825 forces inserter tangs 888 to move away from each other and retracting elongated member 825 allows inserter tangs 888 to move toward each other. In the example shown in FIG. 10C, elongated member 825 can be advanced inside elongated portion 820 of inserter component 800 by turning knob 840 in a direction indicated by arrow 112. The advancement of elongated member 825 forces inserter tangs 888 to move away (i.e., spread) from each other in a direction as indicated by arrow 114 in FIG. 10D. Inserter tangs 888 can have threaded, textured or rough surfaces to further prevent undesirable movement of implant 200 relative to inserter tangs 888. FIG. 10D depicts a top view of implant 200 fully engaged with inserter tangs 888 of inserter component 800 through collar 900. In embodiments disclosed herein, collar 900 is selected so that body 910 of collar 900 is taller than implant 200. In this way, collar 900 can shield implant 200 from compression loading until implant 200 is properly delivered to a desirable location within the intervertebral disc space.

Figure 11A:
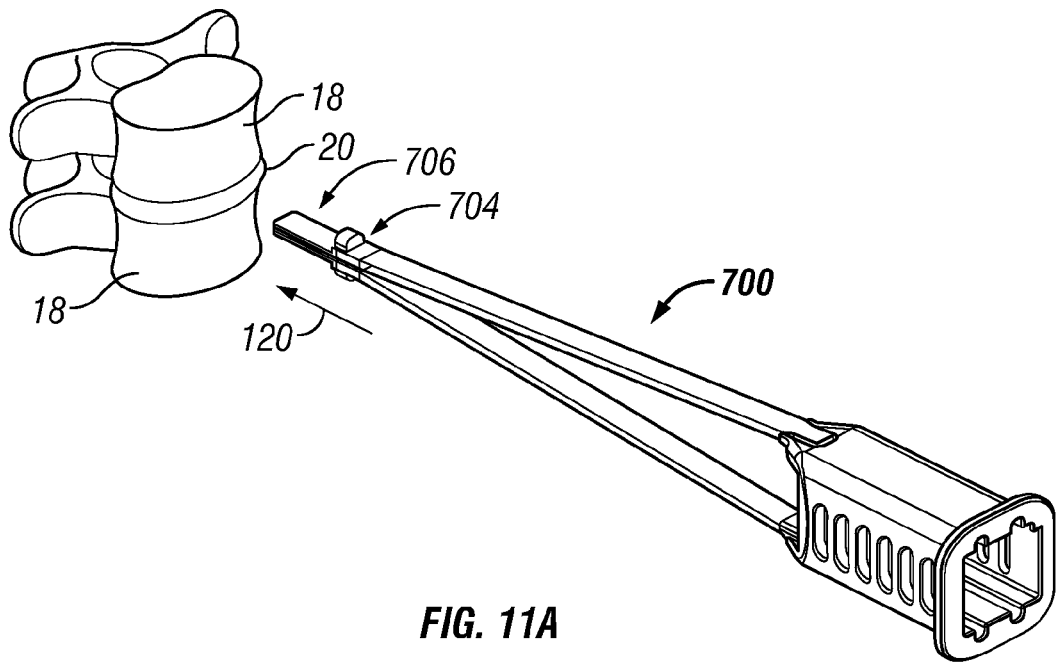
FIGS. 11A-11B illustrate one way of placing a distractor component of a geared spinal implant distractor-inserter instrument between adjacent vertebrae.
Figure 11B:
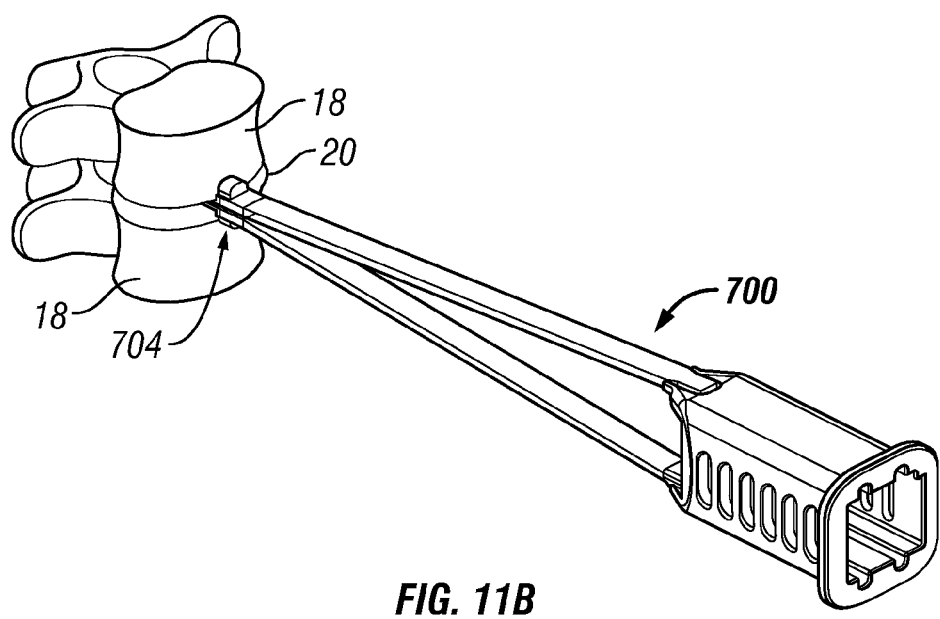

In some embodiments, a method of delivering an intervertebral implant can include fitting a distractor component of an embodiment of a geared spinal implant inserter-distractor disclosed herein in a collapsed disc space between adjacent vertebrae. FIGS. 11A-11B illustrate one way of placing distractor component 700 between adjacent vertebrae 18 in the treatment of intervertebral disc 20. In this case, tips 706 of distractor component 700 are advanced through an incision (not shown) towards intervertebral disc 20 in a direction as indicated by arrow 120 in FIG. 11A. In some embodiments, the position of stops 704 of distractor component 700 may be adjustable. In some embodiments, stops 704 of distractor component 700 are not adjustable. FIG. 11B illustrates that distractor component 700 may be advanced until stops 704 contact or touch vertebrae 18. In the example of FIG. 11B, tips 706 of distractor component 700 extend fully into a space between vertebrae 18. Intervertebral disc 20 may be partially or completely removed prior to insertion of tips 706 of distractor component 700.

Figure 12A:
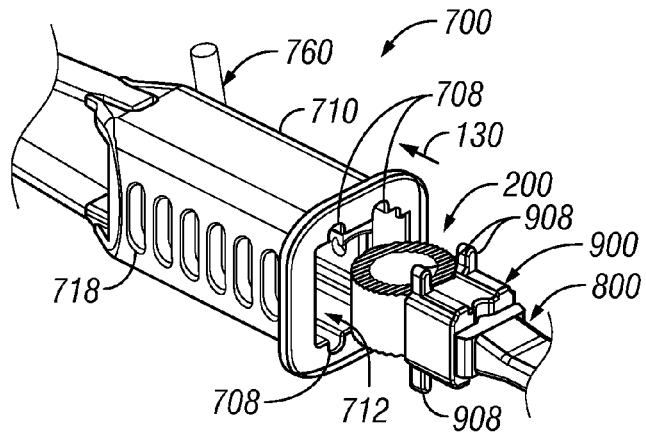
FIGS. 12A-12C illustrate one way of delivering, through the distractor component shown in FIGS. 11A-11B, the interbody implant coupled to the inserter component via the collar as shown in FIGS. 10A-10D.
Figure 12B:
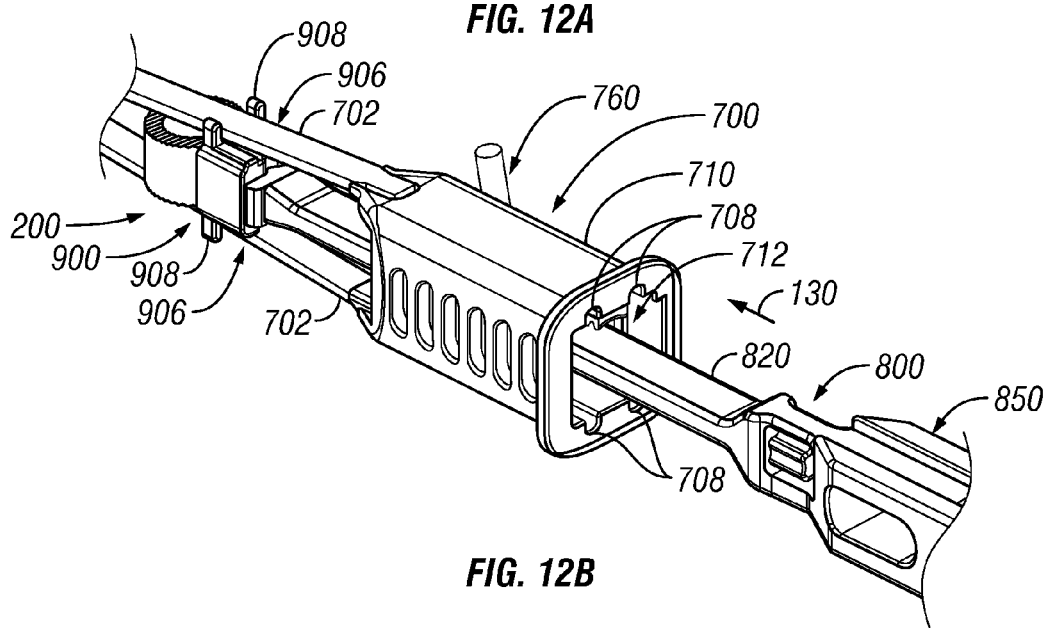
Figure 12C:
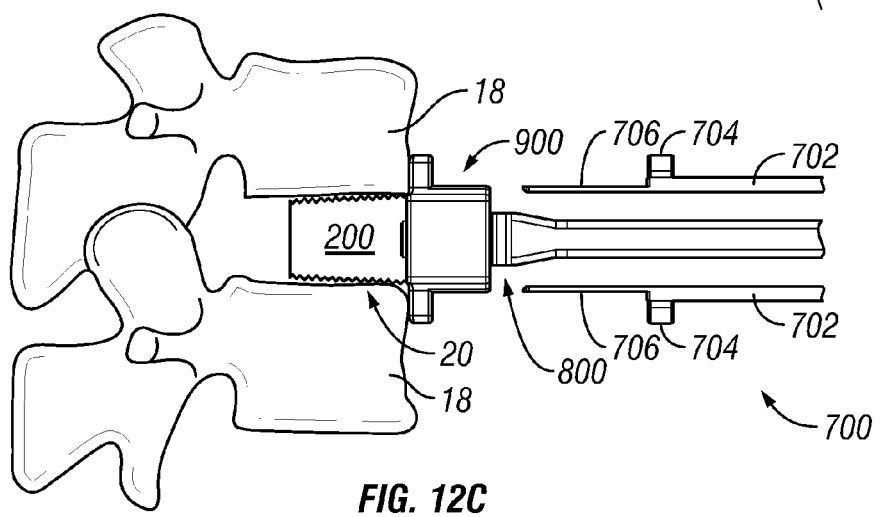

FIGS. 12A-12C illustrate one way of delivering, through distractor component 700 shown in FIGS. 11A-11B, implant 200 held by inserter component 800 and shielded by collar 900 as shown in FIGS. 10A-10D. As shown in FIG. 12A, implant 200 held by inserter component 800 and shielded by collar 900 is fed through opening 712 of distractor component 700 in a direction as indicated by arrow 130.

In FIGS. 12A and 12B, body 710 of distractor component 700 has a plurality of windows 718. Windows 718 can reduce the weight of distractor component 700 and provide visibility of inserter component 800 as well as the geared mechanism to the surgical personnel. Windows 718 can be optional.

As implant 200 held by inserter component 800 and shielded by collar 900 is fed through opening 712 of distractor component 700, channel features 708 of distractor component 700 mate with ears 908 of collar 900 and guide collar 900 towards ramps 702 upon existing body 710. As can be seen in FIG. 12B, protruding features or ears 908 and indentations or channels 906 of collar 900 are structured to accommodate the width of ramps 702 and thus keeping implant 200 aligned with inserter component 800 and distractor component 700. As inserter component 800 is advanced through opening 712 of distractor component 700, body 910 of collar 900 pushes against ramps 702 which, in turn, opens tips 706 of distractor component 700 and distracts vertebrae 18.

As inserter component 800 advances, rack 850 enters opening 712 of distractor component 700 and engages gear 770 which is coupled to handle 760. Although handle 760 is shown in FIGS. 12A and 12B, a detachable embodiment of handle 760 may not need to be attached until rack 850 on inserter component 800 engages gear 770 inside distractor component 700. Once the geared mechanism is engaged, the surgical personnel can turn handle 760 to continue advancing inserter component 800 in the direction as indicated by arrow 130. As described above, the mechanical advantage of the geared mechanism allows the surgical personnel to control the advancement of inserter component 800, along with collar 900 and implant 200 coupled thereto, in a controlled, quantifiable manner. Specifically, rack 850 moves, perhaps one tooth at a time, in the direction as indicated by arrow 130 as handle 760 turns gear 770 inside distractor component 700. The surgical personnel can continue to advance inserter component 800, along with collar 900 and implant 200 coupled thereto, and gradually distracting vertebrae 18 until protruding features or ears 908 of collar 900 touch or contact vertebrae 18. At this point, vertebrae 18 are distracted by tips 706 to a height defined by body 910 of collar 900 as it pushes against ramps 702 of distractor component 700. Since body 910 is selected so that it is taller than the maximum height of implant 200, vertebrae 18 are effectively distracted by tips 706 of distractor component 700 to form an intervertebral disc space that can sufficiently accommodate implant 200. As tips 706 carry much of the compression loading at this point, the surgical personnel can adjust and verify, perhaps through fluoroscopy, the position of implant 200. In some cases, the linear position of implant 200 can be adjusted by turning knob 840 of inserter component 800 as described above.

After determining that implant 200 has been delivered to a proper location between vertebrae 18, the surgical personnel can remove distractor component 700 by turning handle 760 in the opposite direction from what was done to insert implant 200. The geared mechanism, to which handle 760 is coupled, enables distractor component 700 to back out, eventually withdrawing tips 706 as shown in FIG. 12C. Inserter component 800 can then be removed by turning knob 840 to close inserter tangs 888 which, in turn, releases inserter tangs 888 from hole 210 of implant 200. Since tip 818 of inserter component 800 can fit tightly inside opening 912 of collar 900 and inserter component 800 and collar 900 have mating features 894 and 914 to prevent unwanted movements, collar 900 can be retrieved together with inserter component 800 once inserter tangs 888 are released from implant 200. The intervertebral implant thus delivered can restore lumbar disc height and ease lower back pain in the treatment of diseased or degenerative discs.

Embodiments of a surgical instrument useful for delivering a spinal implant in the treatment of a diseased and/or degenerative disc have now been described in detail. Further modifications and alternative embodiments of various aspects of the disclosure will be apparent to those skilled in the art in view of this description. Accordingly, this description is to be construed as illustrative only and is for the purpose of teaching those skilled in the art the general manner of carrying out the disclosure. It is to be understood that the forms of the disclosure shown and described herein are to be taken as examples of embodiments Elements and materials may be substituted for or implemented from those illustrated and described herein, as would be apparent to one skilled in the art after having the benefit of the disclosure. Changes may be made in the elements or to the features described herein without departing from the spirit and scope of the disclosure as set forth in the following claims and their legal equivalents.

What is claimed is:

1. A geared spinal implant inserter-distractor, comprising:
   an inserter component having:
      a toothed bar thereon; and
      an end portion for engaging an intervertebral implant;
   a distractor component having:
      a body having an opening structured to receive the inserter component;
      a pair of ramps extending from the body of the distractor component; and
      a gear therein for engaging the toothed bar on the inserter component inside the distractor component;
   a stub that protrudes from the distractor component and that is connected to the gear inside the distractor component; and
   a handle or a knob coupled to the stub for rotating the stub to turn the gear inside the distractor component, wherein when the toothed bar on the inserter component is engaged with the gear inside the distractor component, turning the handle or the knob relative to the distractor component drives the inserter component in a linear motion.

2. The geared spinal implant inserter-distractor of claim 1, wherein the handle or the knob is detachable from the stub.

3. The geared spinal implant inserter-distractor of claim 2, wherein the handle is a hex driver or a wrench.

4. The geared spinal implant inserter-distractor of claim 1, wherein the distractor component further comprises tips and stops located between the tips and the pair of ramps.

5. The geared spinal implant inserter-distractor of claim 1, wherein the inserter component further comprises a body portion, a neck portion, an elongated portion, and an opening extending through the body portion, the neck portion, and the elongated portion about a central axis thereof.

6. The geared spinal implant inserter-distractor of claim 5, wherein the inserter component further comprises a turn knob and an elongated member positioned inside the elongated portion, wherein the elongated member comprises a threaded end, a shaft, and a tapered end, and wherein the elongated member is coupled to the turn knob at the threaded end.

7. The geared spinal implant inserter-distractor of claim 6, wherein the end portion of the inserter component further comprises inserter tangs and wherein turning the turn knob causes the inserter tangs to spread or close.

8. The geared spinal implant inserter-distractor of claim 7, wherein the intervertebral implant further comprises a hole, wherein turning the turn knob in a first direction causes the inserter tangs to close and fit inside the hole of the intervertebral implant, and wherein when the inserter tangs are inside the hole of the intervertebral implant, turning the turn knob in a second direction causes the inserter tangs to spread and hold the intervertebral implant in position by tension.

9. The geared spinal implant inserter-distractor of claim 5, wherein the inserter component further comprises a flange located between the end portion and the elongated portion.

10. The geared spinal implant inserter-distractor of claim 1, further comprising:
    a collar having:
       a body structured to accommodate the end portion of the inserter and the intervertebral implant; and
       protruding features extending from the body of the collar.

11. The geared spinal implant inserter-distractor of claim 10, wherein the inserter component further comprises a tip portion and wherein the body of the collar further comprises an opening dimensioned to fit the tip portion of the inserter component.

12. The geared spinal implant inserter-distractor of claim 10, wherein the body of the collar further comprises indentations or channels structured to guide and keep the pair of ramps of the distractor component in alignment.

13. A geared spinal implant inserter-distractor, comprising:
    an inserter component having:
       a toothed bar thereon; and
       an end portion for engaging an intervertebral implant;
    a distractor component having:
       a body having an opening structured to receive the inserter component;
       a pair of ramps extending from the body of the distractor component; and
       a gear therein for engaging the toothed bar on the inserter component inside the distractor component;
    a stub that protrudes from the distractor component and that is connected to the gear inside the distractor component;
    a handle or a knob coupled to the stub for rotating the stub to turn the gear inside the distractor component, wherein when the toothed bar on the inserter component is engaged with the gear inside the distractor component, turning the handle or the knob relative to the distractor component drives the inserter component in a linear motion; and
    a collar having:
       a body comprising structured to accommodate the end portion of the inserter and the intervertebral implant; and
       protruding features extending from the body of the collar to guide and keep the pair of ramps of the distractor component in alignment.

14. The geared spinal implant inserter-distractor of claim 13, wherein the inserter component further comprises:
    inserter tangs; and
    a tip portion, wherein the body of the collar further comprises an opening dimensioned to fit the tip portion of the inserter component and allow the inserter tangs to protrude from the tip portion of the inserter component.

15. The geared spinal implant inserter-distractor of claim 13, wherein the distractor component further comprises tips and stops located between the tips and the pair of ramps.

16. The geared spinal implant inserter-distractor of claim 13, wherein the inserter component further comprises a body portion, a neck portion, an elongated portion, and an opening extending through the body portion, the neck portion, and the elongated portion about a central axis thereof.

17. The geared spinal implant inserter-distractor of claim 16, wherein the inserter component further comprises:
- a flange located between the end portion and the elongated portion;
- a turn knob; and
- an elongated member positioned inside the elongated portion, wherein the elongated member comprises a threaded end, a shaft, and a tapered end, and wherein the elongated member is coupled to the turn knob at the threaded end.

18. The geared spinal implant inserter-distractor of claim 17, wherein the end portion of the inserter component further comprises inserter tangs and wherein turning the turn knob causes the inserter tangs to spread or close.

* * * * *